(12) United States Patent
Davis et al.

(10) Patent No.: US 6,635,254 B2
(45) Date of Patent: Oct. 21, 2003

(54) SURFACE MODIFICATION OF LAMELLAR PARTICLES

(75) Inventors: Stanley Stewart Davis, Nottingham (GB); Andrew Wells, Nottingham (GB)

(73) Assignee: West Pharmaceutical Services Drug Delivery & Clinical Research Centre Limited, Nottingham (GB)

( * ) Notice: Subject to any disclaimer, the term of this patent is extended or adjusted under 35 U.S.C. 154(b) by 0 days.

(21) Appl. No.: 09/948,319

(22) Filed: Sep. 6, 2001

(65) Prior Publication Data

US 2002/0068091 A1 Jun. 6, 2002

Related U.S. Application Data

(63) Continuation of application No. PCT/GB00/00755, filed on Mar. 3, 2000.

(30) Foreign Application Priority Data

Mar. 6, 1999 (GB) .............................. 9905136

(51) Int. Cl.[7] .............................. A61K 39/38

(52) U.S. Cl. ............................ 424/184.1; 424/184.1; 424/489; 424/499; 424/501

(58) Field of Search .................. 424/489, 450, 424/400, 426, 184.1, 283.1, 504, 499

(56) References Cited

U.S. PATENT DOCUMENTS 5,665,428 A * 9/1997 Cha et al. ................. 427/213.3
5,840,341 A   11/1998 Watts et al.
5,855,904 A * 1/1999 Chung et al. ............... 424/426

FOREIGN PATENT DOCUMENTS

| WO | WO 95/35097 A1 | 12/1995 | |
| WO | WO 96/01695 A1 | 1/1996 | |
| WO | WO 97/02810 A2 | 1/1997 | |
| WO | WO 97/02810 * | 1/1997 | ............ A61K/9/16 |
| WO | WO 99/06026 A1 | 2/1999 | |

OTHER PUBLICATIONS

Deasy, *Microencapsulation and Related Drug Processes*, Contents, pp. vii–x, (1984).
Pitard et al., "Virus–sized self–assembling lamellar complexes between plasmid DNA and cationic micelles promote gene transfer" *Proc. Natl. Acad. Sci. USA*, vol. 94, pp. 14412–14417, (1997).
Jabbal–Gill et al., "Potential of polymeric lamellar substrate particles (PLSP) as adjuvants for vaccines", *Vaccine*, vol. 18, pp. 238–250, (2000).
Khairullah et al., "Preparation Of Polymeric Lamellar Substrate Particles Of Specific Size Ranges As Poential New Adjuvants", *Proceed. Int'l. Symp Controlled Release Bioact. Mater.*, vol. 27, pp. 323–324, (2000).

* cited by examiner

*Primary Examiner*—Thurman K. Page
*Assistant Examiner*—Micah-Paul Young
(74) *Attorney, Agent, or Firm*—Akin, Gump, Strauss, Hauer & Feld, L.L.P.

(57) ABSTRACT

Lamellar particles are provided comprising a biodegradable and biocompatible polymer and carrying a cationic charge on their surface. These particles are prepared by mixing a preformed negatively charged lamellar particle with a positively charged material. Compositions using these particles may include genetic material or antigens, for example, and may be used as a drug delivery system, such as a sustained release system.

11 Claims, 8 Drawing Sheets

SURFACE MODIFICATION OF LAMELLAR PARTICLES

CROSS-REFERENCE TO RELATED APPLICATION

This application is a continuation of International Application No. PCT/GB00/00755, filed Mar. 3, 2000, the disclosure of which is incorporated herein by reference, which was published in the English language on Sep. 14, 2000, under International Publication No. WO 00/53230.

BACKGROUND OF THE INVENTION

The present invention relates generally to positively charged lamellar particles and to methods for preparing such particles. More specifically, the present invention relates to lamellar particles formed from a biodegradable and biocompatible polymer and which carry a cationic charge on their surface, to compositions containing these particles, and to methods for preparing such particles and compositions.

Lamellar particles prepared by the controlled precipitation of crystalline polymers such as poly-L-lactide (PLA) and polybetahydroxybutyrate (PHB) have been described in PCT International Publication No. WO 96/01695. These particles have been termed polymeric lamellar substrate particles (PLSP). Due to a large surface area and a relatively hydrophobic surface these particles can be used to adsorb antigenic materials, such as influenza vaccine and tetanus toxoid, and have been shown to have utility as vaccine adjuvants. The term "adjuvant" refers to a material that can be added to a vaccine formulation in order to improve the immune response. The lamellar particles can be prepared in different sizes (length and thickness). The surfaces of the lamellar particles can be modified by conditioning the particles, for example by storing them in a buffer solution for a period of weeks. The surface of the particle undergoes polymer degradation resulting in altered antigenic adsorption and release properties. The adsorption properties of the lamellar particles can be characterized by the measurement of an adsorption isotherm. When prepared from polymers such as poly-L-lactide the lamellar particles carry a net negative charge as measured, for example using the method of particle electrophoresis using a Malvern Zeta Sizer 4 (laser doppler anemometry). While such a negative charge can be advantageous for the sorption of certain antigens (particularly when the antigen carries a net positive charge under the conditions adopted for antigen loading), in other situations the net negative charge can be disadvantageous.

A particular problem arises when it is desired to use the lamellar particles for the delivery of polynucleotides (antisense agents and DNA). Polynucleotides carry a net negative charge due to the presence of phosphate groupings. The adsorption of polynucleotides to lamellar particles is very poor due to electrostatic charge repulsion. It would be advantageous to have lamellar particles that carry a net positive charge. It will be appreciated by the person skilled in the art that lamellar particles carrying a net positive charge could also be useful for the delivery of vaccine antigens that were negatively charged, i.e., acidic proteins where adsorption could be effected at pH conditions below the isoelectric point of the antigen.

We have found that it has not previously been possible to produce lamellar particles with a strong positive charge that remains on the particles. We have coated negatively charged lamellar particles produced from poly-L-lactide with an adsorbed cationic material, for example a cationic surfactant, such as cetyltrimethyl ammonium bromide, or a cationic polymer, such as chitosan (polyglucosamine), diethylaminoethyl dextran (DEAE-dextran), or polyethyleneimine. It is possible thereby to change the negatively charged lamellar particles into positive particles, as measured by particle electrophoresis. Unfortunately, the positively charged material is not strongly adsorbed to the particle surface and has a poor stability. The adsorbed cationic material is sensitive to centrifugation, dialysis and high concentrations of electrolyte. With the effect that much of the positively charged material is desorbed or washed off the surface of the particle. This presents a significant problem in further processing, such as particle clean-up and polynucleotide adsorption.

BRIEF SUMMARY OF THE INVENTION

It is therefore an object of the present invention to provide lamellar particles with a positive charge which remains on the particles and a method for producing such particles. The present applicant has developed a novel method of producing positively charged lamellar particles.

The method of the invention may provide positively charged lamellar particles wherein the loss of surface attached material during subsequent processing (e.g., during clean-up and polynucleolide adsorption) is substantially reduced as compared to particles that are surface modified by a simple coating (physisorption process).

According to the present invention, there are also provided compositions comprising lamellar particles which carry a cationic charge on their surface.

In a preferred embodiment the present invention provides compositions comprising lamellar particles which carry a cationic charge on their surfaces and a material, for example genetic material.

DETAILED DESCRIPTION OF THE INVENTION

The cationic charge on the lamellar particles typically arises from a cationic material attached to or incorporated into the particles. The positively charged lamellar particles are typically produced by co-precipitation of the particles in the presence of a cationic material. The cationic polymer is preferably adsorbed to the surface of the lamellar particle.

The particles of the present invention carry a net positive charge, and the loss of surface-attached material during subsequent processing, such as clean-up and polynucleolide adsorption, is substantially reduced as compared to particles that are surface-modified by a simple coating (physisorption process).

The amount of surface attached-material that is lost during processing can be evaluated in a quantitative fashion. The surface charge (zeta potential, measured in mV) on the lamellar particles suspended in a buffer of low ionic strength is measured using the technique of particle electrophoresis.

Preferably, cleaning of the particles, such as by the addition of aqueous buffer or water and recovery of the 'washed' particles by centrifugation or filtration should not result in a greater than 80% loss of surface charge as measured by particle electrophoresis in the same buffer of low ionic strength. More preferably, such loss of charge should be less than 50% of that for the unwashed particles and, most preferably, less than 35% of the value for unwashed particles.

The lamellar particles of the invention may be prepared from any biodegradable and biocompatible polymer. Suitable polymers are preferably crystalline.

We use the term "biodegradable polymer" to include polymeric systems at least a part of which can degrade into low molecular weight compounds which are known to be involved normally in metabolic pathways. We also use the term to include polymer systems which can be attacked in the biological milieu, so that the integrity of the system, and in some cases of the macromolecules themselves, is affected and gives fragments or other degradation by-products which can move away from their site of action, but not necessarily from the body.

The biodegradable polymer used is preferably at least 5 percent by weight crystallizable.

The biodegradable polymer in the particles is preferably at least 5 percent by weight crystalline, more preferably at least 30%, more preferably at least 50%, still more preferably at least 70%, and most preferably at least 90% crystalline.

Whether or not a polymer is crystalline, and the degree of crystallinity, can be determined by methods well known in the art, for example X-ray diffraction methods as applied to polymers or by differential scanning calorimetry.

Suitable polymers for use in the particles of the present invention include poly-L-lactide (PLA) and polyalkanoic acids, such as polyhydroxybutyrate (PHB) and polyhydroxyvalerate (PHV).

The polymer may be a mixture of PLA with another biodegradable polymer or with a biocompatible but non-degradable polymer, either as a copolymer or as a blend of polymers. In either case, the resulting mixture should still be at least in part crystalline and preferably at least 5% by weight crystalline. The content of a non-crystallizable or non-crystalline polymer component should therefore be limited as necessary.

Suitable copolymers are copolymers of PLA and other poly($\alpha$-hydroxy acids), such as DL lactide or glycolide (e.g., PLG), crystallizable copolymers of lactic acid and lactone, copolymers of L-lactide and poly(ethylene glycol) [PEG], copolymers of L-lactide and $\alpha$-amino acids (polydepsipeptides), polyanhydrides, and polyorthoesters.

Suitable blends of PLA with other polymers include other poly($\alpha$-hydroxy acids) such as poly(DL lactide co-glycolide), PEG, copolymers of polyethylene oxide and polypropylene oxide (PEO-PPO), polydepsipeptides, polyorthoesters, polyanhydrides, polyphosphazene and copolymers of acrylic and methacrylic acid esters (Eudragit®).

Other biodegradable synthetic polymers potentially useful for preparing lamellar substrates include copolymers of $\alpha$-hydroxy acids, $\alpha$-amino acids (polydepsipeptides), polyhydroxybutyric acid, copolymers of lactic acid and lactone, copolymers of lactic acid and PEG, copolymers of hydroxybutyrate and hydroxyvalerate, polyethylene terephthalate, polyphosphazenes, polycarprolactone, polyorthoesters, polyanhydrides and copolymers thereof, or blends of such polymers. By "lamellar" we means that the particles comprise thin plates or layers; liposomes are not lamellar particles of the invention. It is preferred if the lamellar particles are irregularly shaped as may be formed using some of the methods in the Examples.

The lamellar particles are often "lozenge-shaped", and may be present in the compositions as discrete lamellar particles, or as sheave-like, polyhedral particles formed by lamellae which are coalesced together along a common plane. The term "lamellar particle" is used to include both possibilities. The surface of the lamella often exhibits a stepped topography which is typical of polymer crystal growth.

The particle morphology can be measured using scanning electron microscopy and atomic force microscopy.

Poly-L-lactide polymers that are suitable for use in the particles have molecular weights of from 1 kd to 1000 kd. Poly-L-lactide polymers with molecular weights of from 1 kd to 100 kd are preferred, and poly-L-lactide polymers with molecular weights of from 1 kd and 10 kd are especially preferred.

Polyalkanoic acids suitable for use in the particles have molecular weights of from 10 kd to $10^6$ kd. Polyalkanoic acids with molecular weights of from $10^3$ kd to $10^5$ kd are preferred.

The lamellar particles of the present invention typically have a mean size (length) across the largest dimension of from 0.1 $\mu$m to 100 $\mu$m. Lamellar particles with a mean size of from 0.2 $\mu$m to 50 $\mu$m are preferred and lamellar particles with a mean size of from 0.5 $\mu$m to 10 $\mu$m are especially preferred.

The mean thickness of the lamellar particles of the invention is typically from 0.05 $\mu$m to 10 $\mu$m. Lamellar particles with a mean thickness of from 0.1 $\mu$m to 1 $\mu$m are preferred.

Cationic polymers suitable for use in the particles of the present invention include polygalactosamine, chitosan, DEAE-dextran, polyethyleneimines, polyamidoamines, polyaminoacids (polylysine, polyornithine), cationic guars and cationic starches.

Preferred cationic polymers include polyethyleneimine polymers. These polymers can be readily protonated to form highly charged cationic polymers.

Polyethyleneimines are obtained through the polymerization of the ethylenimine monomer. Some of these materials have been known as process chemicals under the name Polymin®. The BASF company produces a range of PEI materials under the trade name Lupasol®. They are available in molecular weights from 25 kd to 750 kd. At a pH value of 4.00 about 50% of the amine functions are protonated. The charge density on PEI polymers is from 15 to 20 meq/g.

Polyethyleneimines with molecular weights of from 10 kd to 100 kd are preferred. Polyethyleneimines with molecular weights of from 20 to 40 kd are especially preferred.

Lamellar particles obtained by the co-precipitation of polyethyleneamines (PEI) are positively charged and the particles maintain a positive surface charge even after repeated washing.

The concentration of cationic polymer in the particles may be from 1% to 99%. The concentration of cationic polymer in the particles is preferably from 5 to 90%. An especially preferred concentration of cationic polymer in the particles is from 10 to 80%.

The surface charge on the cationic lamellar particles may be from +1 mV to +150 mV, as measured at pH 7.4 at 25° C. in a medium of low ionic strength (0.001 M). A preferred surface charge on the cationic particles is from +10 mV to +70 mV.

The lamellar particles of the present invention can be used as biodegradable particulate carriers. The present invention therefore also provides compositions comprising the lamellar particles and another material, for example a genetic material. Typically the material to be carried binds/adsorbs onto the surface of the preformed lamellar particle. Such compositions have potential to be versatile DNA delivery systems.

Suitable materials includes antigens, drugs and genetic material, such as polynucleotides.

Antigens include polypeptides, proteins, glycoproteins and polysaccharides that are obtained from animal, plant, bacterial, viral and parasitic sources or produced by synthetic methods. We use the term antigen to include any material which will cause an antibody reaction of any sort when administered. Such antigens can be administered by injection or to various mucosal sites (nasal, oral, vaginal, rectal, colonic).

Similarly, certain drugs could be adsorbed to lamellar particles and then delivered to a specific site in the body using the lamellar particle as a carrier. The lamellar particle could also be used to provide a sustained release system for a drug. The lamellar particles can be delivered by injection (intravenous, subcutaneous, intramuscular, intraperitoneal, etc.) or to a mucosal surface (gastrointestinal tract, buccal cavity, eye, vagina, nose, rectum). The particles could also be delivered into the skin using a needleless injector in the form of a suspension or as a powder.

The particles could also be used to facilitate wound healing. For example, an agent useful in wound healing such as a growth factor could be adsorbed to the particles. Particles having such adsorbed agents could be applied to wounds.

The particles are preferably prepared by a method known as non-solvent induced precipitation. Suitable solvents and non-solvents will depend on the nature of the polymer. Solvents and non-solvents which are suitable for a particular polymer will be readily identifiable to a person of ordinary skill in the art. Acetone is a preferred solvent for the polymer (e.g., PLA) and the non-solvent is typically water or an aqueous solution.

The particles may be prepared by dissolving the polymer (e.g., PLA) in an organic solvent, for example acetone or tetrahydrofuran (THF) and dissolving the cationic polymer in water. The aqueous cationic solution is added dropwise to the stirred organic polymer solution.

The mixture is then left to stir for 10 to 12 hours under ambient conditions. The particles are collected by centrifugation (at, for example, 5000 rpm for 5 mins) and washed with water (typically three times).

The particles may alternatively be prepared by dissolving the polymer (e.g., polyhydroxybutyrate) in an organic solvent, for example dichloromethane or chloroform, and dissolving the cationic polymer in a non-aqueous solvent which is a non-solvent for the first polymer, for example methanol, ethanol, propan-2-ol, acetone, isopentane, or hexane. Other potential non-solvents include ethyl acetate, xylene and dioxane. The organic cationic mixture is then left to stir for 10 to 12 hours under ambient conditions. The particles are collected by centrifugation and washed with water or a non-aqueous non-solvent for the first polymer.

Heat may be applied to dissolve the polymer in the solvent, if necessary.

It will be clear to the skilled person that for some polymers it is appropriate to use an aqueous non-solvent, while for other polymers it is more appropriate to use a non-aqueous non-solvent.

By "non-solvent" we mean a solvent in which the polymer has a low or negligible solubility so that the polymer will come out of solution as a (partly) crystalline material (precipitation process). The solvents and non-solvents for polymers can be found in standard texts (e.g., see Fuchs, in *Polymer Handbook*, 3rd Edition) and Deasy, *Microencapsulation and Related Drug Processes,* Marcel Dekker, Inc., New York (1984).

The ability of a polymer to dissolve in a solvent can be estimated using the Cohesive Energy Density Concept (CED) and related solubility parameter values as discussed by Deasy and in detail in the article by Grulke in *Polymer Handbook*. Thus a person skilled in the art will be able to select a "non-solvent" to give the required precipitation of the lamellar material.

The lamellar particles may also be made by a crystallization method in which the polymer is dissolved in the solvent as before, cooled and left to crystallize. The particles can then be harvested by filtration.

Material may be adsorbed to the particles by a process of simple admixture of a suspension of the lamellar particles and a solution of the material. The material is preferably dispersed in water. The amount of lamellar particles is selected to provide complete adsorption of the material as indicated by the measurement of an adsorption isotherm for the system. For example, this method may be used to adsorb genetic material, such as DNA (e.g., plasmid DNA), to the particles. Typically 0.5 mg of lamellar particles can be used to adsorb 100 µg of plasmid DNA.

The lamellar particles and the compositions may be used for the delivery of a polynucleotide, vaccine or drug. The lamellar particles and the compositions may also provide a sustained release system for a drug.

The particles and compositions of the invention may be administered to a patient in any suitable manner known in the art. For example, the particles and compositions may be formulated for administration by injection, parenterally, nasally or orally.

The particles and compositions of the present invention may be formulated for injection, for example for intramuscular, intravenous, subcutaneous, intraarticular or intraperitoneal injection. They will generally be sterile and pyrogen-free. The particles and compositions may be adapted for administration to the dermal or epidermal layer of the skin by injection or needleless injector system. The particles and compositions may also be adapted for administration to mucosa, such as the nose, the gastrointestinal tract, the colon, the vagina and the rectum. The particles and compositions of the invention may also be applied to wounds. The particles and compositions may be applied to a wound by any suitable method known in the art.

The particles and compositions of the invention can be formulated in ways well known in the art. The formulations may conveniently be presented in unit dosage form and may be prepared by any of the methods well known in the art of pharmacy. Such methods include the step of bringing the particles or compositions into association with a suitable carrier. In general the formulations can be prepared by uniformly and intimately bringing the particles or compositions into association with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use.

Extemporaneous injection solutions and suspensions may be prepared from sterile powders, granules and tablets of the kind previously described.

Preferred unit dosage formulations are those containing a daily dose or unit, daily sub-dose or an appropriate fraction thereof, of an active ingredient.

It should be understood that in addition to the ingredients particularly mentioned above the formulations of this invention may include other agents conventional in the art having regard to the type of formulation in question.

The amount of the particles or compositions of the invention to be administered to a patient may be determined in relation to the amount of material to be administered, to the amount of material present in the composition, and to the way in which the active agent becomes available in the patient following administration.

Suitably, the amount of the composition administered would be that which contains from 1% to 1000% of the normal amount of the active agent administered to the patient when administered in a conventional way. Preferably, the amount is from 10% to 500% of the normal amount of the active agent; more preferably from 80 to 205%.

For nasal administration, the particles can be administered as a fine suspension using a spray device or if in the form of a powder using a powder device or nasal insufflator. Such devices are familiar to those skilled in the art. Formulations for the gastrointestinal tract (oral administration) can be administered as suspensions or solutions or formulated as tablets, capsules or into compressed or extruded pellets.

For material that is sensitive to the acid conditions in the stomach the delivery system can be protected by an enteric polymer familiar to those skilled in the art of formulation. The enteric polymer can be used to coat the dosage form. Vaginal systems suitable for delivery include gels and vaginal suppositories. Rectally administrated vaccines can be given as enemas or incorporated into suppositories.

BRIEF DESCRIPTION OF THE SEVERAL VIEWS OF THE DRAWINGS

The foregoing summary and detailed description of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

SPECIFIC EXAMPLES

The present invention is now illustrated, but not limited, by reference to the following examples.

Example 1
Preparation and Characterization of Lamellar Particles (a) A general method for the preparation and characterization of lamellar particles produced from PLA is provided. PLA (molecular weight 2 kd from Polysciences, USA) (100 mg) was dissolved in 5 ml acetone (HPLC grade) (Fisher Scientific, UK) to produce a 2% w/v (2 g in 100 ml) solution. The chosen cationic polymer was accurately weighed and dissolved in double distilled water (10 ml) to produce a fixed concentration solution. The PLA solution was magnetically stirred and the cationic polymer solution was added dropwise allowing time for each drop to equilibrate with the PLA solution. The mixture was left to stir for 12 hours under ambient conditions. The particles were collected by centrifugation at 5000 rpm for 5 minutes in a Beckman centrifuge and washed with distilled water three times. These positively charged lamellar particles are termed pos-PLSP. The particles can be suspended to a required concentration in the buffer of choice.

(b) Similar lamellar particles were produced but without the addition of the cationic polymer to the water phase. These negatively charged lamellar particles are termed neg-PLSP.

(c) Lamellar particles produced without the addition of cationic polymer were suspended in an aqueous solution containing from 0.1% to 25% w/v of cationic polymer, and the particles washed after incubation for 1 to 2 hours. These particles are termed negatively charged PLSP particles rendered positive by subsequent adsorption of cationic material (neg-PLSP-pos).

Measurement of Surface Charge—Malvern Zeta Sizer 4 (Malvern Instruments, UK)

The electrophoretic mobility of the particles was measured using Malvern Zetasizer 4 in 1 mM Hepes Buffer (pH 7.4). A fat emulsion (Intralipid™) dispersed in Hepes buffer was used to check the calibration of the equipment. Each sample was prepared in Hepes buffer and injected into the cell. Four scans were conducted on each sample and the average and standard deviations recorded. Samples were prepared and analyzed in duplicate.

Measurement of Particle Size—Malvern Mastersizer (Malvern Instruments, UK)

Lamellar particles (20 to 50 mg) were dispersed into 1 ml of double distilled water. The sample was dispersed under moderate stirring and the particle diffraction measured as a function of particle size using a Malvern Mastersizer with a 45 mm focal lens and distilled water as a background. The volume mean diameter D (v 0.5), the D (v 0.9) and the D (v 0.1) values were all recorded.

The Effect of Subsequent Washing of Lamellar Particles on Surface Charge

Particles were prepared as described above with different cationic polymer solutions of polyethyleneimine (BASF) molecular weight 25 kd (10 mg/ml), chitosan (grade 210 Pronova, Norway) (5 mg/ml) and DEAE dextran (Sigma) (10 mg/ml). The resulting particles were washed several times with distilled water, and samples removed after each washing for measurement of surface charge using the Zetasizer.

Example 2
The Stability of Cationic Lamellar Systems to Desorption of Attached Cationic Materials When cationic polymers were physically adsorbed to preformed negatively charged PLSP particles (neg-PLSPpos) the cationic materials were found to significantly desorb from the particle during washing and centrifugation, exposure to high concentrations of dissolved salts or even dialysis over time. This presented the significant problem of separating surface bound coating from unbound coating. Table 1 shows the differences in zeta potential for negative PLSP particles (neg-PLSP), PLSP particles coated with the cationic surfactant centrimide (neg-PLSP-pos) and particles prepared using the cationic polymer polyethyleneimine (pos-PLSP).

TABLE 1

Surface Charge and Particle Size Data for PLSP Systems.

| | Potential (mV) | | | Particle Size (μm) | | |
|---|---|---|---|---|---|---|
| Formulation | Unwashed | Washed x3 | NaCl Wash | D (v0.1) | D (v0.5) | D (v0.9) |
| Neg-PLSP | −38.2 | −41.3 | −39.5 | 2.13 | 5.58 | 21.44 |
| Neg-PLSP-Pos | +13.1 | −32.4 | −36.1 | N/A | N/A | N/A |
| Pos-PLSP | +34.5 | +26.3 | +25 | 3.92 | 7.7 | 14.74 |

N/A—Not available

The above results illustrate that the lamellar particle produced by co-precipitation of the particles in the presence of the cationic material have enhanced surface entrapment of cationic polymer and reduced desorption of the coating during clean up processes.

Figure 1:
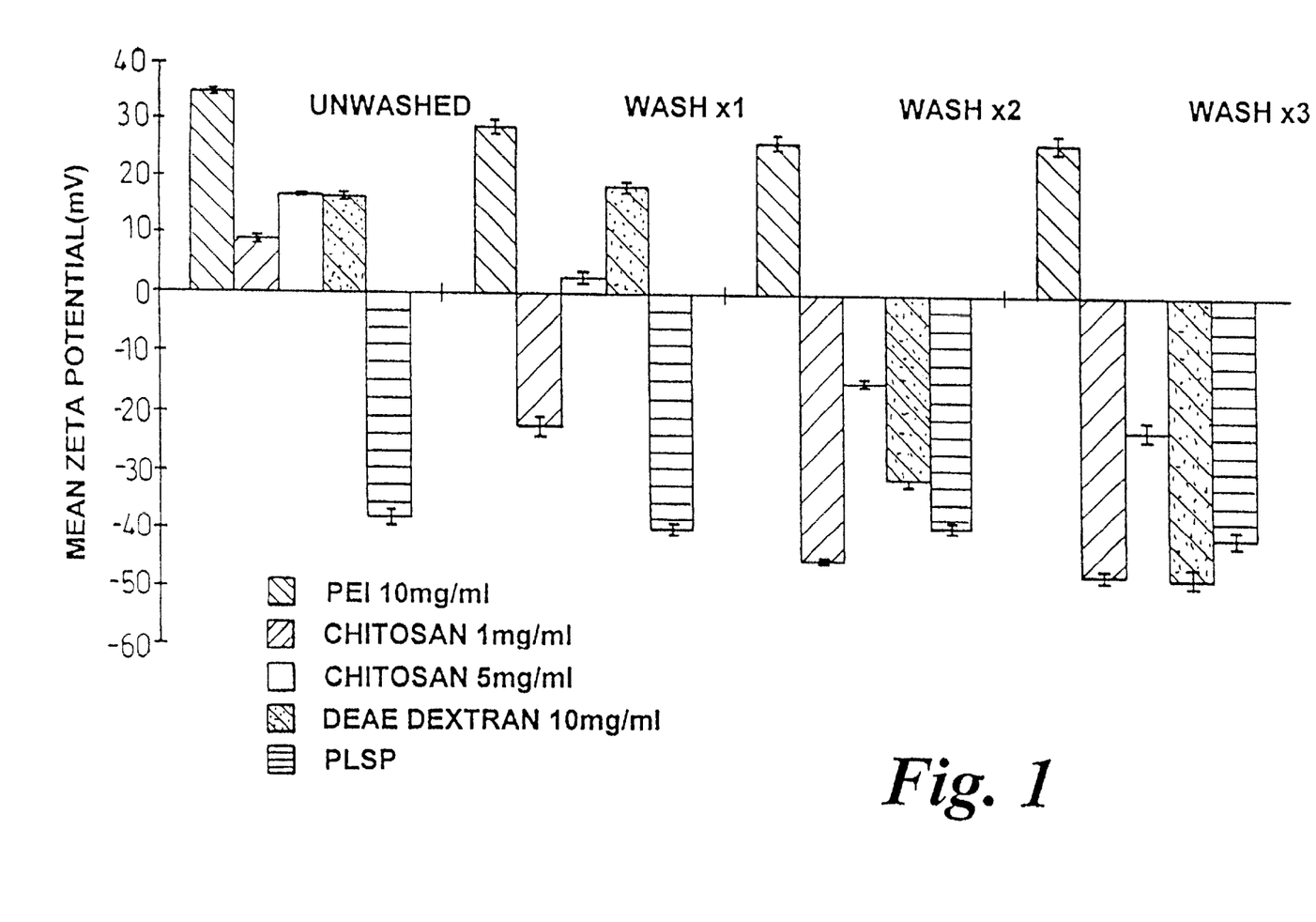
FIG. 1 is a bar graph showing the effect of washing particles on the surface charge on lamellar particles.

Lamellar particles (pos-PLSP) were prepared from poly-L-lactide in the presence of polyethyleneimine (PEI), chitosan and DEAE dextran as described in Example 1(a). These particles had an initial positive charge as shown in FIG. 1. (The Fig. also shows data for the standard PLSP system with a negative charge). However, upon subsequent washes, the surface charge of the lamellar particles made with chitosan and the DEAE dextran was reduced. This is an indication of desorption of some of the cationic polymer from the surface of the particles. Although the surface charge for chitosan/PLA lamellar particles declined after one wash, it did not reach the value for unmodified PLA lamellar particles. This is an indication of incomplete desorption for these polymers, and there may be a proportion of adsorbed cationic polymer remaining.

The PEI lamellar particles maintained a positive charge throughout repeated washings. This suggests that the PEI was strongly sorbed on the particle surface and resistant to centrifugal forces and the washing procedure. It is postulated that the branched nature of the PEI polymer and high cationic charge density contribute to the attachment of this material on the PLA particle surface. These particles were identified as suitable for further investigation.

Example 3
The Effect of Storage on the Surface Charge on PEI/PLA Lamellar Particle PEI/PLA lamellar particles were prepared as in Example 1(a) and stored as an aqueous suspension at room temperature for 7 days. Samples were removed on day 0, 1, 2 and 7 for measurement of surface charge using the Malvern Zetasizer.

Figure 2:
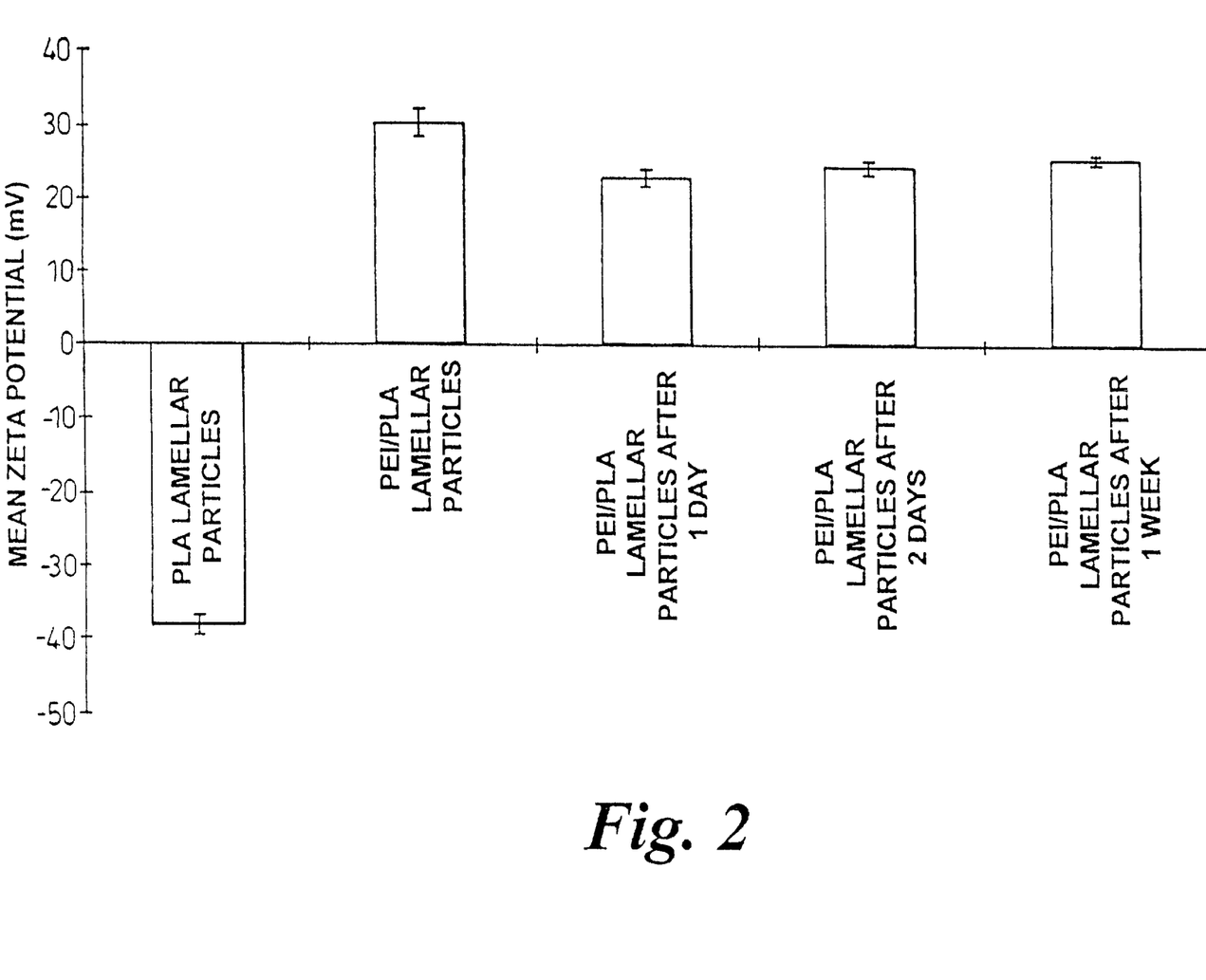
FIG. 2 is a bar graph showing the effect of time on the surface charge on PEI/PLA lamellar particles.

The result of the charge analysis of the particles demonstrated the stability of the PEI/PLA formulation over time as shown in FIG. 2.

Example 4
The Effect of Sodium Chloride Washings on the Surface Charge of PEI/PLA Lamellar Particles PEI/PLA lamellar particles, prepared as above in Example 1(a), were washed with saturated NaCl solutions followed by distilled water. Samples were removed for measurement of surface charge.

Figure 3:
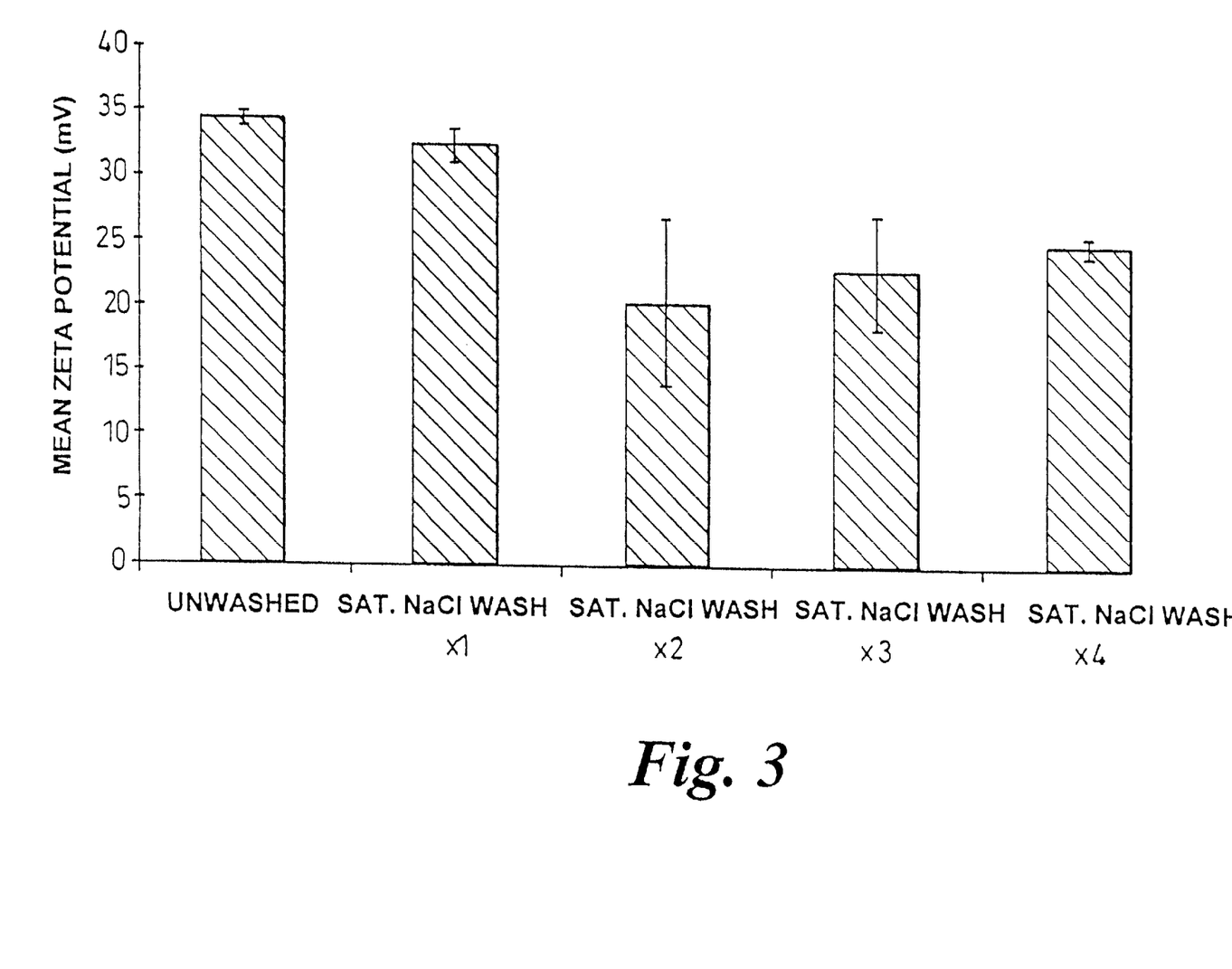
FIG. 3 is a bar graph showing the effect of saturated sodium chloride washes on the surface charge on PEI/PLA lamellar particles.

Exposure to high salt concentration, which is known to disrupt electrostatic binding, did not significantly alter the adsorption of the cationic polymer as shown in FIG. 3. The stability of the PEI coating in these conditions could indicate that entrapment of the polymer in the particle is occurring rather than solely electrostatic adsorption.

Example 5
The Effect of PEI Concentration on the Surface Charge of PEI/PLA Lamellar Particles PEI/PLA lamellar particles were prepared, as above in Example 1(a), except that the concentration of PEI employed in the process was varied between batches. PEI solutions of 0, 0.1, 0.25, 0.5, 0.75, 1, 5 and 10 mg/ml were used and the surface charge of the washed particles determined. Batches were prepared in duplicate.

Figure 4:
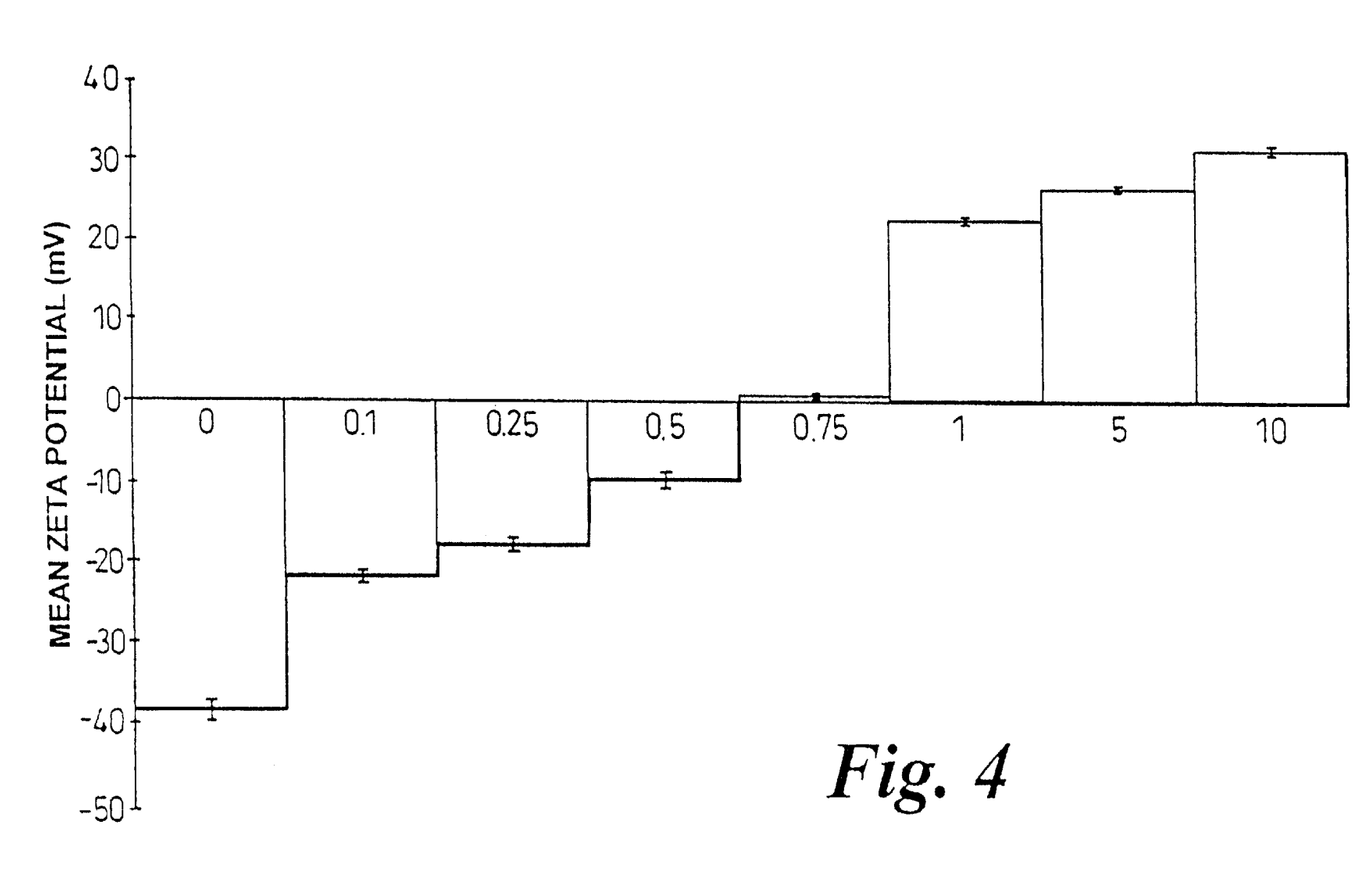
FIG. 4 is a bar graph showing the effect of PEI concentration on the surface charge on PEI/PLA lamellar particles.

The effect of the PEI concentration during the particle manufacture governed the resulting particle surface charge, as shown in FIG. 4. The system therefore possesses a versatility to provide particles of varying surface charge, which may be of value when differential adsorption is required.

Example 6
Particle Size Analysis of PEI/PLA Lamellar Particles

Figure 5:
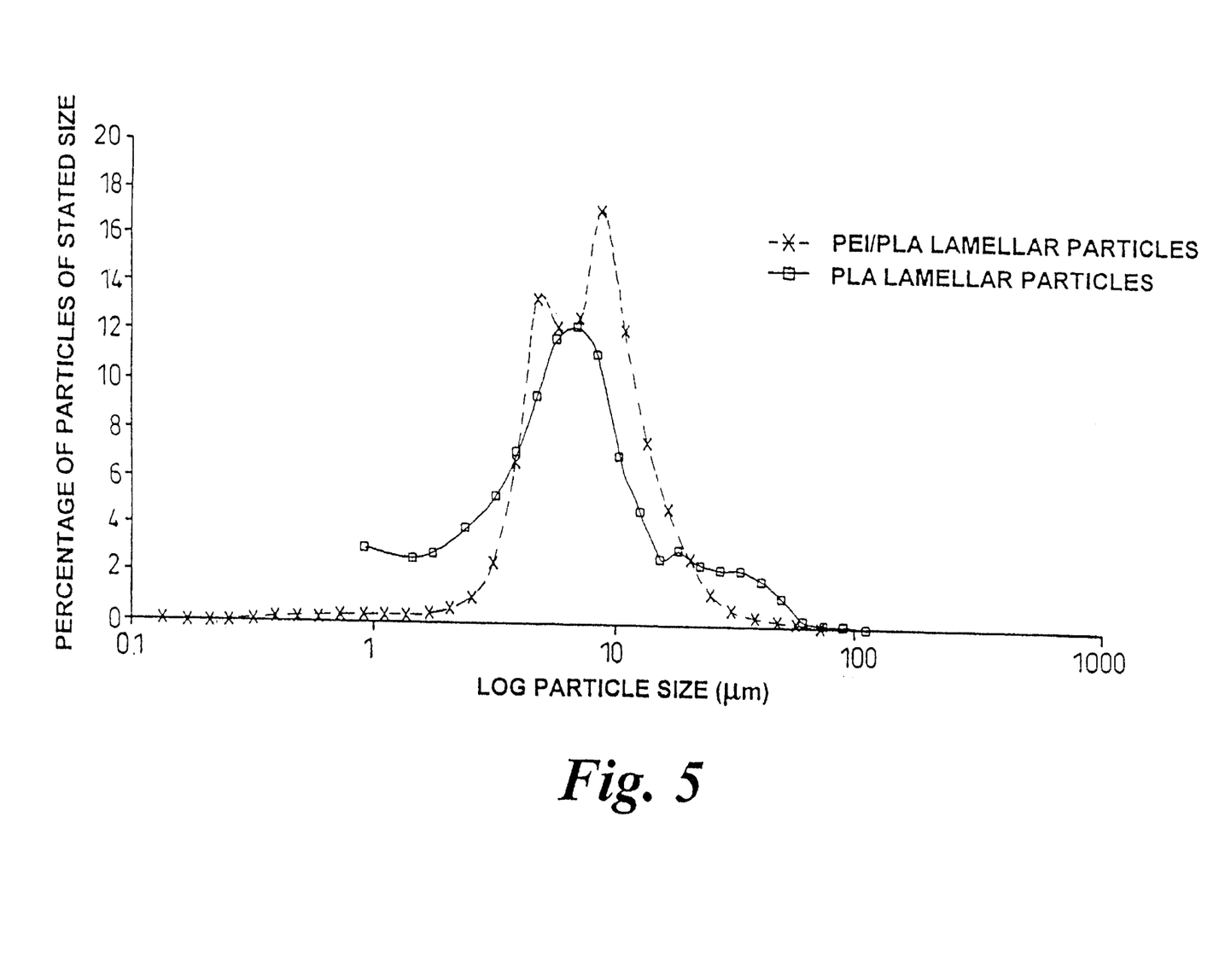
FIG. 5 is a graph showing the particle size distribution of PEI/PLA lamellar particles and PLA lamellar particles.

The particle size distribution as shown in FIG. 5 indicates that the majority of the particles were within the size range of 0 to 10 μm known to be the optimum for uptake at mucosal surfaces. This allows the delivery of DNA to mucosal surfaces using these particles; an ideal property for mucosal DNA vaccination.

Example 7
Binding of Polynucleotide to Cationic Lamellar Particles
Agarose Gel Electrophoresis Retardation Assay of Plasmid (pCMV-β-Gal) DNA Interaction with PEI/PLA Lamellar Particles An agarose gel electrophoresis assay was used to study the interaction between plasmid DNA and the PEI/PLA lamellar particles. A gel bed of 0.8% agarose in 1×TAE buffer containing 1 μg/ml ethidium bromide was prepared. DNA-PEI/PLA lamellar particle samples were prepared containing 1 μg of plasmid DNA (pCMV-β-Gal, 7.2 kB, from Therexsys, UK) and PEI/PLA lamellar particles varying from 0 to 160 μg.

A general method for incubating DNA with PLSP is as follows:

PLSP is diluted to a suitable concentration, e.g., 4 mg particles/ml. An aqueous buffer or distilled water is placed into a sterile plastic sample tube. DNA is added from a known concentration stock solution to produce the required concentration in the sample tube and briefly vortexed to allow thorough mixing. PEI/PLA lamellar particles (nominally 0.5 mg/125 μl) are added to the sample tube from the stock solution under moderate stirring to ensure a constant particle distribution.

Samples are loaded into the gel wells in a volume of 5 μl. The gel is run at 60 V for 1 to 1.5 hours immersed in 1×TAE buffer. Photographs are obtained by UV translumination with an aperture of 5.6 and 1 second exposure. The potential use of these particles as carriers of genetic material is clearly demonstrated using plasmid DNA adsorption onto the particles visualised using agarose gel electrophoresis.

Figure 6:
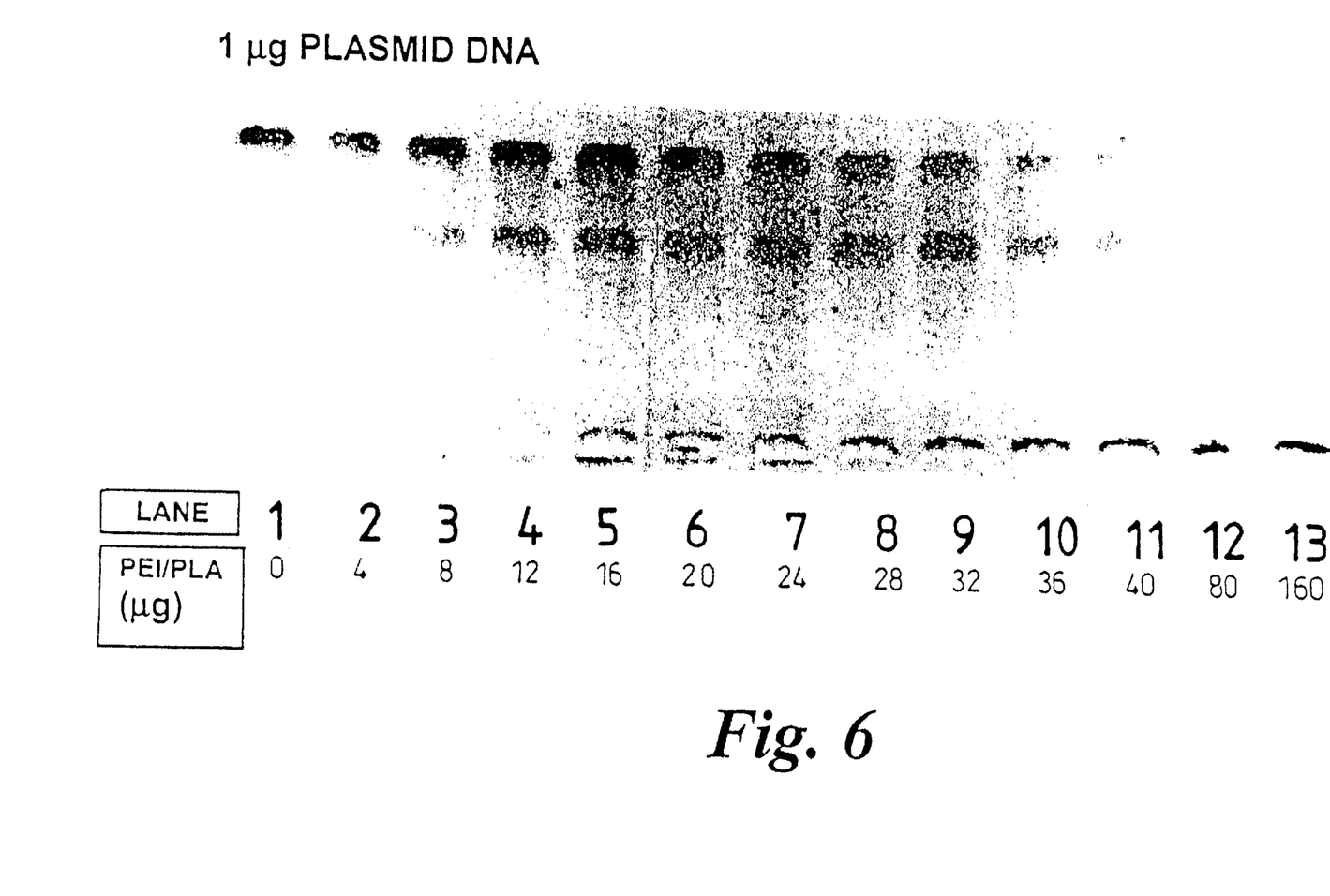
FIG. 6 shows the results of an agarose gel electrophoresis assay conducted on mixtures of plasmid DNA and PEI/PLA lamellar particles.

FIG. 6 shows an example of such an experiment where the different numbers correspond to different quantities of added PEI/PLA particles (μg).

Plasmid DNA loaded into the gel wells migrates in the applied electric field towards the positive electrode due to the negative charge of the DNA molecule. The extent that the plasmid DNA traverses the agarose gel bed depends on a number of factors namely the size and conformation of the plasmid DNA.

It can clearly be seen in FIG. 6 that two bands are visible. The band farthest from the gel well is supercoiled DNA which travels the furthest by virtue of the compacted nature of the plasmid allowing greater passage through pores in the agarose gel bed. The band nearer the well corresponds to relaxed circular plasmid where, due to the open conformation of the plasmid and hence the larger size, the plasmid DNA has traversed the gel bed to a lesser degree. It is evident that as the concentration of PEI/PLA lamellar particles is increased the amount of plasmid DNA leaving the gel well is reduced due to the adsorption of DNA to the particle surface. The DNA particle conjugate is too large to exit the well and contributes to the fluorescence emanating from the well.

Complete retardation of the plasmid traversing the agarose gel occurs with 40 to 80 μg of PEI/PLA lamellar particles. This corresponds to the complete formation of particle DNA complex with 1 μg plasmid DNA.

Example 8

Isotherms for Plasmid DNA Adsorption on to PEI/PLA Lamellar Particles

Duplicate 125 μl (0.5 mg) samples of a PEI/PLA lamellar particle stock solution (4 mg/ml) were incubated with varying concentration of plasmid DNA (pCMV-β-Gal) from 0.5 to 100 μg. The samples were filtered through a 0.45 μm filter and the filtrate collected for UV analysis at 260 nm. Control samples of DNA only and particles only were used as controls for each DNA concentration tested. The results are expressed as the equilibrium concentration against the DNA loading onto the PEI/PLA lamellar particles.

Figure 7:
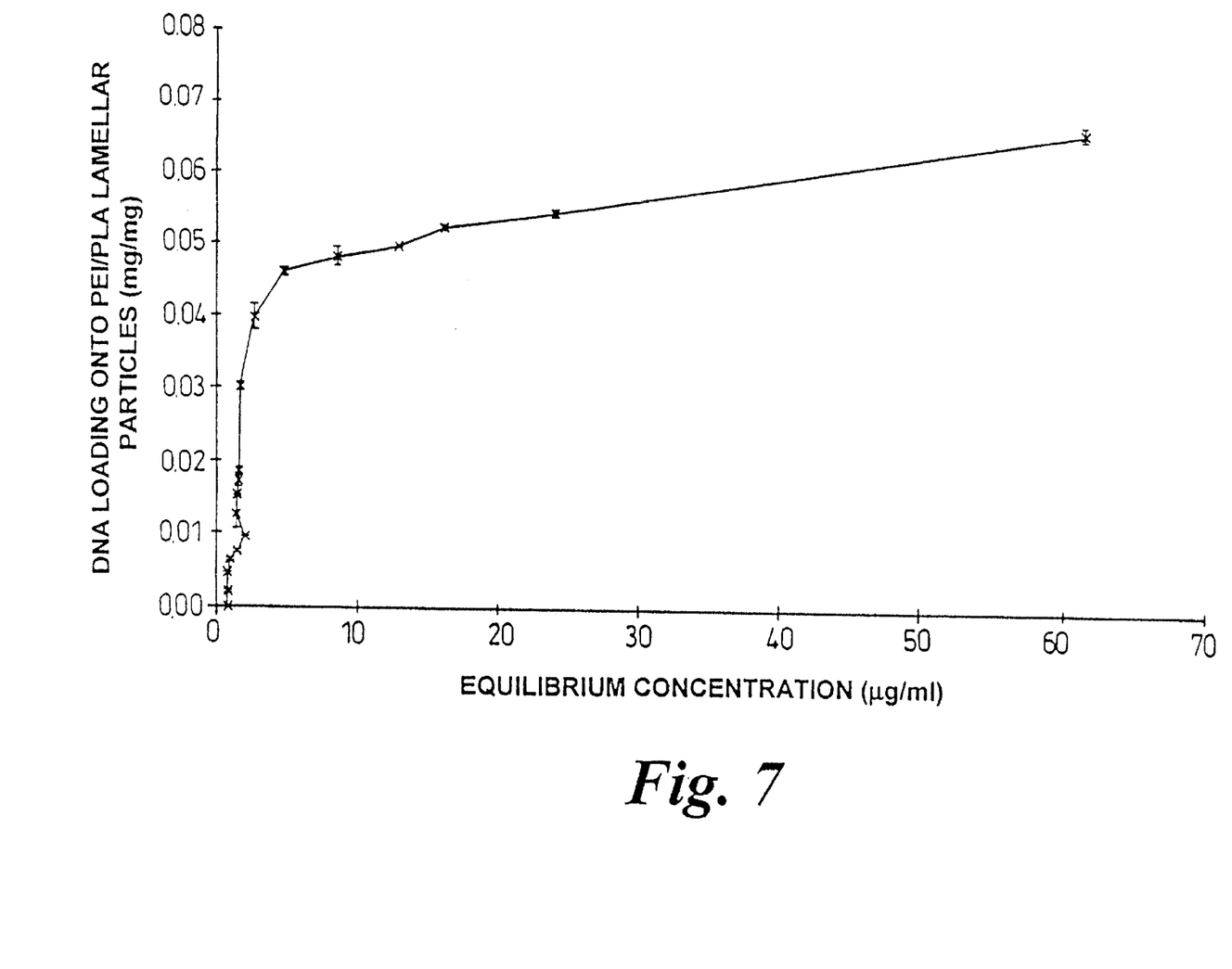
FIG. 7 is a graph showing the adsorption isotherm for the uptake of plasmid DNA on to PEI/PLA lamellar particles.

The affinity isotherm for plasmid DNA and the PEI/PLA lamellar particles is shown in FIG. 7. The DNA adsorption conforms to a typical high affinity isotherm with saturation of 500 μg of lamellar particles occurring at a level of 0.05 mg plasmid DNA/mg particles. At higher concentrations of DNA there is a slight increase in the amount of loading onto the particles. A possible reason for this would be quenching of the particle charge by adsorbed DNA reducing the attractive force for the more DNA adsorption.

In a comparative test there was no significant adsorption of DNA to negatively-charged lamellar particles.

Example 9

The Effect of DNA Adsorption on PEI/PLA Lamellar Particle Surface Charge

Figure 8:
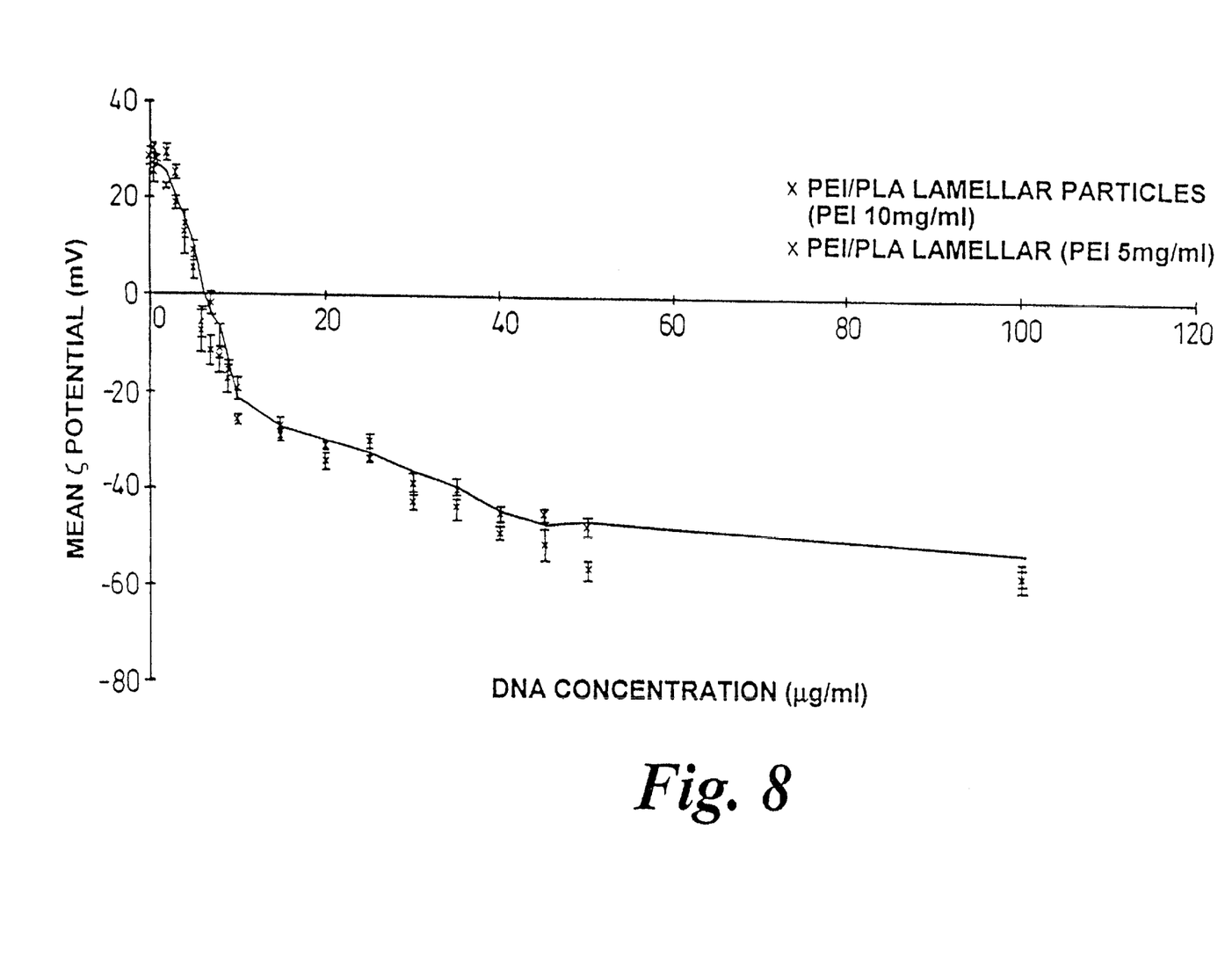
FIG. 8 is a graph showing the effect of DNA concentration on the surface charge carried by PEI/PLA lamellar particles.

Duplicate 125 μl (0.5 mg) samples of a PEI/PLA lamellar particle stock solution (4 mg/ml) were incubated with varying concentrations of DNA from 0.5 to 100 μg/ml. The resulting samples were suspended in 1 mM Hepes buffer for surface charge analysis. The results are shown in FIG. 8.

The initial surface charge of the PEI/PLA lamellar particles is +27.8 mV (10 mg/ml PEI) and +28.5 mV (5 mg/ml PEI). The addition of DNA, which binds to the surface of the positively charged particle, neutralizes the surface charge towards 0 mV. The subsequent addition of more DNA increases the extent of adsorption and reverses the charge on the particle to a net negative charge. The magnitude of the negative charge increases to around −55 mV at which the saturation of the surface capacity to bind DNA appears to be reached. The results agree with the observations of the adsorption isotherm, Example 8, where the DNA displays an initial high affinity for the particle surface until saturation of the surface occurs and the presence on free "unbound" DNA can be detected. During the initial high affinity stage the particle surface charge reverts from a net positive to a net negative due to the bound DNA.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A lamellar particle which is not a liposome and which comprises a biodegradable and biocompatible polymer and carries a cationic charge on its surface, wherein the cationic charge arises from a cationic material attached to or incorporated into the particle, and the cationic material is selected from the group consisting of DEAE-dextran and polyethyleneimine.

2. The particle according to claim 1, wherein the polymer is poly-L-lactide or a polyalkanoic acid.

3. A method for the preparation of a lamellar particle according to claim 1, comprising mixing a preformed negatively charged lamellar particle with a positively charged material selected from the group consisting of DEAE-dextran and polyethyleneimine.

4. The method according to claim 3, wherein the mixing comprises co-precipitating the preformed negatively charged lamellar particle in the presence of the positively charged material.

5. The method according to claim 4 wherein the co-precipitation step comprises non-solvent induced precipitation.

6. A composition comprising lamellar particles, as defined in claim 1, and genetic material.

7. A composition comprising lamellar particles, as defined in claim 1, and antigen.

8. The composition according to claim 6, wherein the genetic material is a polynucleotide.

9. A method for the preparation of a composition according to claim 6, comprising admixing a suspension of the lamellar particles with a solution of the genetic material or an antigen.

10. A method for the delivery of a polynucleotide, a vaccine, or a drug, comprising combining the polynucleotide, vaccine or drug with a lamellar particle according to claim 1.

11. A sustained release system for a drug comprising a lamellar particle according to claim 1 and the drug.

* * * * *